United States Patent
Reardon (10) Patent No.: US 11,325,060 B2
(45) Date of Patent: May 10, 2022

(54) FILTER APPARATUS AND FILTER DEVICE FOR BIOLOGICAL SAMPLES

(71) Applicant: Apacor Limited, Wokingham (GB)

(72) Inventor: Paul Reardon, Wokingham (GB)

(73) Assignee: Apacor Limited, Wokingham (GB)

( * ) Notice: Subject to any disclaimer, the term of this patent is extended or adjusted under 35 U.S.C. 154(b) by 138 days.

(21) Appl. No.: 16/096,016

(22) PCT Filed: Apr. 26, 2017

(86) PCT No.: PCT/GB2017/051157
§ 371 (c)(1),
(2) Date: Oct. 24, 2018

(87) PCT Pub. No.: WO2017/187165
PCT Pub. Date: Nov. 2, 2017

(65) Prior Publication Data
US 2019/0134541 A1    May 9, 2019

(30) Foreign Application Priority Data

Apr. 26, 2016  (GB) ..................................... 1607245

(51) Int. Cl.
*B01D 29/44*        (2006.01)
*B01D 29/58*        (2006.01)
(Continued)

(52) U.S. Cl.
CPC ........ *B01D 29/445* (2013.01); *A61B 10/0038* (2013.01); *B01D 29/33* (2013.01);
(Continued)

(58) Field of Classification Search
CPC .. A61B 10/0038; B01D 29/33; B01D 29/445; B01D 29/58; B01D 2201/184;
(Continued)

(56) References Cited

U.S. PATENT DOCUMENTS 3,905,895 A    9/1975  Addis
4,068,713 A    1/1978  McGuire
(Continued)

FOREIGN PATENT DOCUMENTS

CN    2457588    10/2001
CN   101542069     9/2009
(Continued)

OTHER PUBLICATIONS

European Patent Office, "International Preliminary Report on Patentability," App. No. PCT/GB2017/051157 (dated Apr. 20, 2018).
(Continued)

*Primary Examiner* — Patrick Orme
(74) *Attorney, Agent, or Firm* — Walters & Wasylyna LLC (57) ABSTRACT

According to at least one aspect, the invention provides a filter assembly (100) comprising a tubular housing and a filter device (70) locatable to extend longitudinally within the housing. The filter device (70) comprises a lattice structure of crossing internal and external elongated elements (18, 20). The lattice structure comprises an arrangement of pores (22), and the external elongated elements (20) are presented outwardly of the filter device (70) with respect to the plane of the pores, thereby to provide ribs on the exterior of the lattice which define a shaped channel that will act as a first level filter for larger particles. The external elongated elements are shaped and arranged to provide one or more additional filter levels for smaller particles in advance of said pores, through which yet even smaller particles may pass.

13 Claims, 10 Drawing Sheets

(51) Int. Cl.
*A61B 10/00* (2006.01)
*G01N 1/40* (2006.01)
*B01L 3/00* (2006.01)
*B01D 29/33* (2006.01)

(52) U.S. Cl.
CPC ............ B01D 29/58 (2013.01); B01L 3/5021 (2013.01); G01N 1/4077 (2013.01); *B01D 2201/184* (2013.01); *B01D 2201/60* (2013.01); *B01L 2300/0681* (2013.01); *G01N 2001/4088* (2013.01)

(58) Field of Classification Search
CPC .... B01L 3/14; B01L 3/502; B01L 2300/0681; B01L 3/5021; B01L 3/50255; G01N 1/4077; G01N 2001/4088
See application file for complete search history.

(56) References Cited

U.S. PATENT DOCUMENTS

| | | | |
|---|---|---|---|
| 4,579,698 | A | 4/1986 | Meyering et al. |
| 5,095,990 | A | 3/1992 | Best et al. |
| 5,556,544 | A | 9/1996 | Didier |
| 6,296,763 | B1 * | 10/2001 | Hicks .................. B01L 3/5021 210/244 |
| 2008/0185349 | A1 | 8/2008 | Willliams |
| 2009/0133874 | A1 * | 5/2009 | Dale ...................... E21B 43/088 166/278 |

FOREIGN PATENT DOCUMENTS

| | | |
|---|---|---|
| CN | 203830027 | 9/2014 |
| CN | 204008178 | 12/2014 |
| CN | 204461803 | 7/2015 |
| CN | 106390569 | 2/2017 |
| GB | 2 321 857 | 5/2000 |
| RU | 98146 | 10/2010 |
| WO | WO 98/34710 | 8/1998 |
| WO | WO 2007/040737 | 4/2007 |

OTHER PUBLICATIONS

Intellectual Property Office, Combined Search and Examination Report, App. No. GB1607245.6 (dated Dec. 22, 2016).
National Institute of Industrial Property (Brazil), translation of Office Action, App. No. BR112018071975-7.
Federal Service for Intellectual Property (Russia), Office Action, App. No. 2018141269/05(068742) (dated Dec. 4, 2019).
China National Intellectual Property Administration, translation of Search Report, App. No. 201780038730.2.
Japan Patent Office, translation of Office Action, App. No. 2018-557039 (dated Nov. 5, 2019).

* cited by examiner

FILTER APPARATUS AND FILTER DEVICE FOR BIOLOGICAL SAMPLES

This application is a U.S. national phase application of Intl. App. No. PCT/GB2017/051157 filed on Apr. 26, 2017, which claims priority from GB1607245.6 filed on Apr. 26, 2016. The entire contents of Intl. App. No. PCT/GB2017/051157 and GB1607245.6 are incorporated herein by reference.

FIELD OF THE INVENTION

The present invention relates to improvements in enclosed filtration assemblies and filter devices therefor, particularly but not exclusively to solvent-free filtration devices for use in both a laboratory and an ambulatory environment. More specifically, but not exclusively, the invention relates to filtration devices used for the separation of parasites from faecal material samples. Advantageously the removal of the need for solvent is an improvement not only to the laboratory but also in the overall manufacturing process. Aspects of the invention relate to a solvent free parasite concentrator or filtration apparatus and to a filter for use therein.

BACKGROUND OF THE INVENTION

It is conventional to examine a faecal biological sample by placing it in a first tubular receptacle which is then closed by a filter medium. The first tubular receptacle may be attached to a second tubular receptacle in axial alignment such that the sample will pass through the filter medium and selectively into the second receptacle. Filtration can be achieved simply by standing the assembly with the first receptacle uppermost or it may be encouraged by shaking the joined receptacles and/or by placing them in a centrifuge. Following the completion of filtration, particles trapped by the filter and/or precipitated to the closed end of the second receptacle can be removed for analysis. In addition centrifugal filtration systems exist to enable rapid separation of the fixed samples utilising solvent (for example ether or ethyl acetate) which is not necessarily regarded as safe for a technician to use.

A double-receptacle filtration system of this kind is particularly suitable for the treatment of faecal samples where it is desired to isolate and remove for analysis of parasites, their eggs and larvae which may be present in the sample. The handling of such samples is unpleasant and presents biological hazards so that the "closed" double-receptacle filtration system is particularly attractive. Hitherto, however, the filter medium used has most commonly been a disc of woven material or a moulded lattice which can be fitted across the open mouth of the first receptacle. This is liable to become clogged and occluded by larger particles suspended in the sample, such as pieces of undigested food Moreover if the double-receptacle is placed in a centrifuge this will tend to drive particles through the filter into the second receptacle. For this reason filtering and centrifuging are normally done separately and this two-stage operation is time consuming and labour intensive, as well as representing a hazard to the operator when the two receptacles are disconnected.

The present invention seeks to provide an improvement in the field of enclosed filtration devices that has particular application for the separation of parasites from faecal material samples. The invention may be utilised in applications other than for the separation of parasites from faecal material samples.

In accordance with the present invention there is provided a filtration assembly comprising a three level stepped and coordinated reduction in porosity in a single element.

The filter provides a greatly enlarged filter area by comparison with a disc filter, but a more important advantage is that centrifugal forces, instead of driving particles through the filter will instead drive them off the filter and toward the shoulder, where they will be retained when the two receptacles are subsequently disconnected. This means that filtration and centrifuging can be carried out as a single operation. There is no danger of contamination of the sample in the second receptacle and the two receptacles can be disconnected without exposing the operator to the residue in the first receptacle.

SUMMARY OF THE INVENTION

Aspects of the invention provide an enclosed filtration apparatus and a filter device for use therein as claimed in the appended claims.

According to one aspect of the invention, there is provided a filter assembly comprising a tubular housing and a filter device locatable to extend longitudinally within the housing, wherein the filter device comprises a lattice structure of crossing internal and external elongated elements, which lattice structure comprises an arrangement of pores, wherein the external elongated elements are presented outwardly of the filter device with respect to the plane of the pores, thereby to provide ribs on the exterior of the lattice which are shaped and arranged to provide a first level filter for larger particles, and wherein the external elongated elements are further shaped and arranged to provide one or more additional filter levels for smaller particles in advance of said pores, through which yet even smaller particles may pass. The external elongated elements being further shaped and arranged by having one or more side walls that are shaped in a stepped, castellated or otherwise graded manner in order to facilitate at least three levels of filtration.

Optionally, the tubular housing comprises a first receptacle for mixing, the first receptacle having an open end and a closed end; and a second receptacle for receiving filtrate, the second receptacle having an open end and a closed end; and wherein the filter device is structured and arranged to be enclosed by said first and second receptacles and wherein the open ends of the first and second receptacles are each closeable by the filter device when located to extend longitudinally therein, such that an enclosed filter assembly is formed.

Optionally, the filter device comprises an open end and a closed end.

Optionally, the lattice structure of crossing internal and external elongated elements comprises internal ribs extending longitudinally in a direction from the closed end of the filter device to the open end of the filter device; and external ribs extending transversely to the internal ribs.

Optionally, said pores of the lattice structure are defined at least in part by said internal ribs.

Optionally, the external ribs extend substantially circumferentially about at least a substantial part of the filter device.

Optionally, between two adjacent external ribs a channel is formed, which channel is defined by parts of each of said two adjacent external ribs, and wherein said channel will act as a first level filter for larger particles and provides one or more additional filter levels for smaller particles in advance of said pores.

Optionally, the external ribs each have two side walls which are each shaped in a stepped manner such that between two adjacent external ribs an opening is formed which has a maximum outer width (a), a minimum inner width (c) and one or more widths between said maximum outer width and said minimum inner width such that the filter assembly is capable of providing at least three levels of filtration.

Optionally, the external ribs each have two side walls which are shaped in a stepped manner such that between two adjacent external ribs an opening is formed which has a maximum outer width (a), a minimum inner width (c) and an intermediate width (b) that is less than said maximum outer width and that is greater than said minimum inner width such that the filter assembly is capable of providing three levels of filtration.

Optionally, the maximum outer width (a) of the castellated opening formed between two adjacent external ribs comprises a first level filter of about 1 mm; the intermediate width (b) of the opening formed between two adjacent external ribs comprises a second level filter of about 440 microns; and minimum inner width (c) of the castellated opening formed between two adjacent external ribs comprises a third level filter of about 220 microns.

Optionally, the external ribs each have two side walls and wherein one side wall is substantially flat, and wherein the other side wall is shaped in a stepped manner such that between two adjacent external ribs an opening is formed which has a maximum outer width (a), a minimum inner width (c) and one or more widths between said maximum outer width and said minimum inner width such that the filter assembly is capable of providing at least three levels of filtration.

Optionally, the external ribs each have two side walls and wherein one side wall is shaped in a first stepped manner, and wherein the other side wall is shaped in a second stepped manner, the two side walls being differently shaped such that between two adjacent external ribs an asymmetric opening is formed which has a maximum outer width (a), a minimum inner width (c) and one or more intermediate widths (b) between said maximum outer width and said minimum inner width such that the filter assembly is capable of providing at least three levels of filtration.

Optionally, because the filter device can close said first and second receptacles, the filter assembly when closed is configured for forced filtration by centrifuge.

Optionally, the filter device comprises a head, a body comprising the lattice structure, and a closing portion structured and arranged for fitting into and closing the open ends of the first and second receptacles, wherein the body comprising the lattice structure has a cross-sectional shape that is generally circular, hexagonal or another polygonal shape.

As described, the filter preferably comprises a three level castellated lattice structure of crossing, elongated elements of which at least those presented outwardly of the filter tube extend outwardly of the filter with respect to the plane of the pores formed by the crossing elements, thereby to provide ribs on the exterior of the lattice which will act as a pre-filter for larger particles in advance of said pores and those acting as a second level pre-filter which in addition removes the need for solvent, for example, to act on any fatty material that is in the sample.

An advantage of this arrangement is that occlusion of part of the length of a channel defined by two adjacent ribs by a large particle will not occlude the pore or pores confronted by the trapped particle, because liquid will still reach said pore or pores along the channel beneath the particle. It has been calculated that particles just large enough to be trapped by the ribs can confront each pore within the lattice without any observable restriction of the flow of liquid through the filter. If the depth of the ribs is increased then larger particles can confront several pores within the lattice without any observable restriction in the flow through the filter.

In a moulded, tubular construction it is preferable that internal ribs extend in a longitudinal manner because otherwise it may be difficult to remove the mould core. Preferably therefore, any external ribs preferably extend in a transverse manner (the outer part of the mould being separated into two halves to remove it from the moulded filter). Transverse external ribs on a tubular filter formation have a dual advantage. During manufacture and while the filter is still contained in the external part of the mould they serve to anchor it while the mould core is withdrawn from the interior of the filter.

When the filter is in use the external ribs being transverse means that the channels formed between them are at right angles to the "natural flow" of the liquid sample out of the first receptacle. This may cause the liquid to change direction to enter the channels and may enhance filtration by creating a greater tendency for larger particles to be trapped by the "pre-filter" channels.

Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. The applicant reserves the right to change any originally filed claim or file any new claim accordingly, including the right to amend any originally filed claim to depend from and/or incorporate any feature of any other claim although not originally claimed in that manner.

BRIEF DESCRIPTION OF THE DRAWINGS

Embodiments of the invention will now be described, by way of example only, with reference to the accompanying drawings, in which:

FIG. 5B is an enlarged view of a portion of a body of the filter device shown in FIG. 5A, the body comprises a lattice structure, and FIG. 5B shows the castellated or stepped side walls of externally and transversally extending elements of the lattice structure;

DETAILED DESCRIPTION OF EMBODIMENTS

Detailed descriptions of specific embodiments of the filter assembly, filter device and methods of the present invention are disclosed herein. It will be understood that the disclosed embodiments are merely examples of the way in which certain aspects of the invention can be implemented and do not represent an exhaustive list of all of the ways the invention may be embodied. Indeed, it will be understood that the filter assembly, filter device and methods described herein may be embodied in various and alternative forms. The figures are not necessarily to scale and some features may be exaggerated or minimised to show details of particular components. Well-known components, materials or methods are not necessarily described in great detail in order to avoid obscuring the present disclosure. Any specific structural and functional details disclosed herein are not to be interpreted as limiting, but merely as a basis for the claims and as a representative basis for teaching one skilled in the art to variously employ the invention.

Figure 7A:
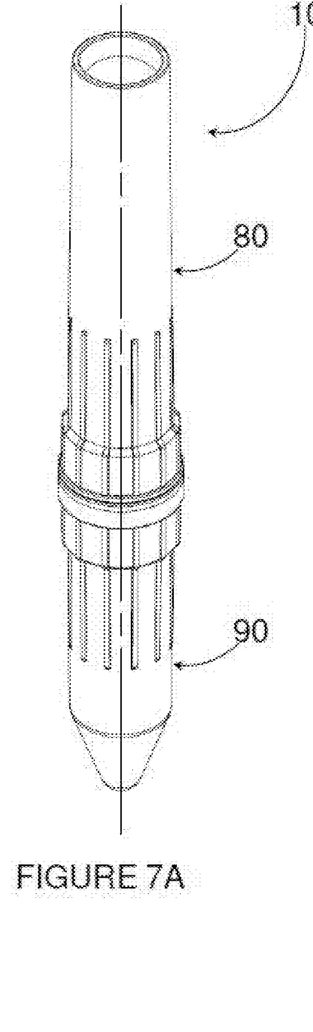
FIGS. 7A and 7B show a filter assembly comprising the filter device of FIGS. 1 to 6B; and comprising a first mixing receptacle and a second filtrate receiving receptacle.
Figure 7B:
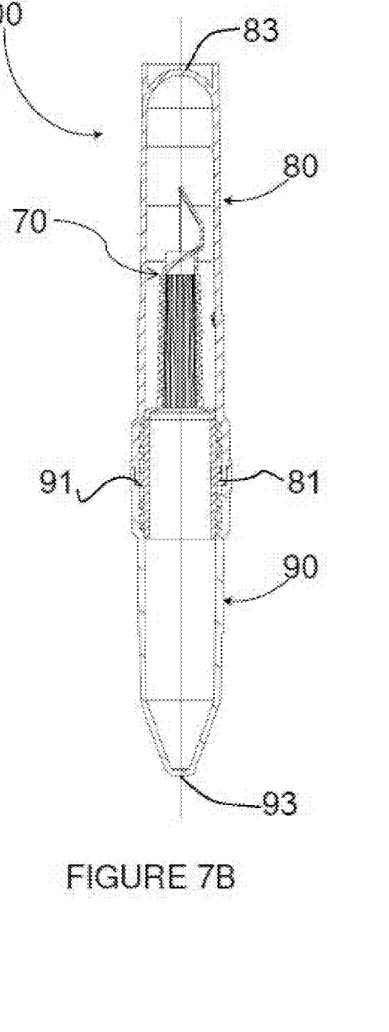
Figure 8:
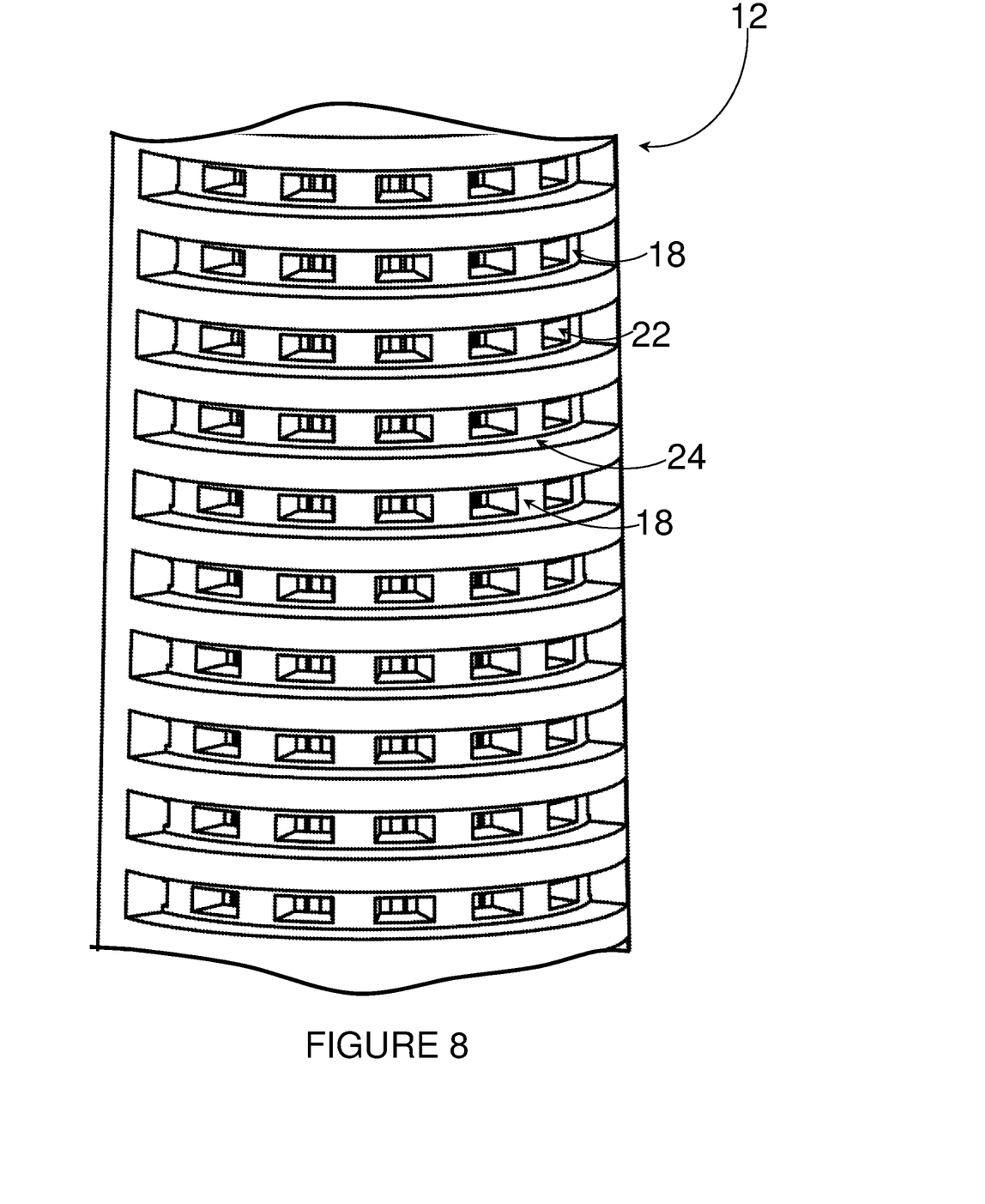
FIG. 8 is an enlarged perspective view of a body of the filter device shown in FIG. 1 showing the lattice structure.

An optional three level, injection moulded, filter assembly 100 is shown in FIGS. 7A and 7B. The filter assembly 100 is for separating out particles from a sample, for example a faecal sample, where it is desired to isolate and remove for analysis of parasites, their eggs and larvae which may be present in the sample. The filter assembly 100 comprises a first receptacle 80, more specifically a mixing receptacle 80 where the sample may optionally be mixed with a reagent or solvent or other liquid. The first receptacle 80 has an open end 81 and a closed end 83. The filter assembly 100 comprises a second receptacle 90 that is for receiving at least part of the filtrate separated from the sample. The second receptacle has an open end 91 and a closed end 93. The filter assembly 100 also comprises a filter device 70.

The filter device 70 may also be referred to as filtration device 70 without imparting any limitation or additional meaning to the term filter device 70. The filter device 70 is shown in FIGS. 1 to 6B. The filter device 70 comprises a generally tubular structure and an optional head 10 (see FIGS. 1, 2 and 3A) which may optionally be in the form of a scoop for conveniently obtaining a sample for analysis. The head 10 provides a closed end for a tubular core of the filter device 70. The filter device 70 has a tubular body 12 and a tubular closure or stopper 14 (shown for example in FIG. 4). The closure 14 is configured such that a shouldered portion extends radially outward from the body 12 and into a flange which can be fitted into, and optionally screw fitted to, the open end of the first receptacle 80; and to the open end of the second receptacle 90. This is best illustrated in FIG. 7B.

Figure 1:
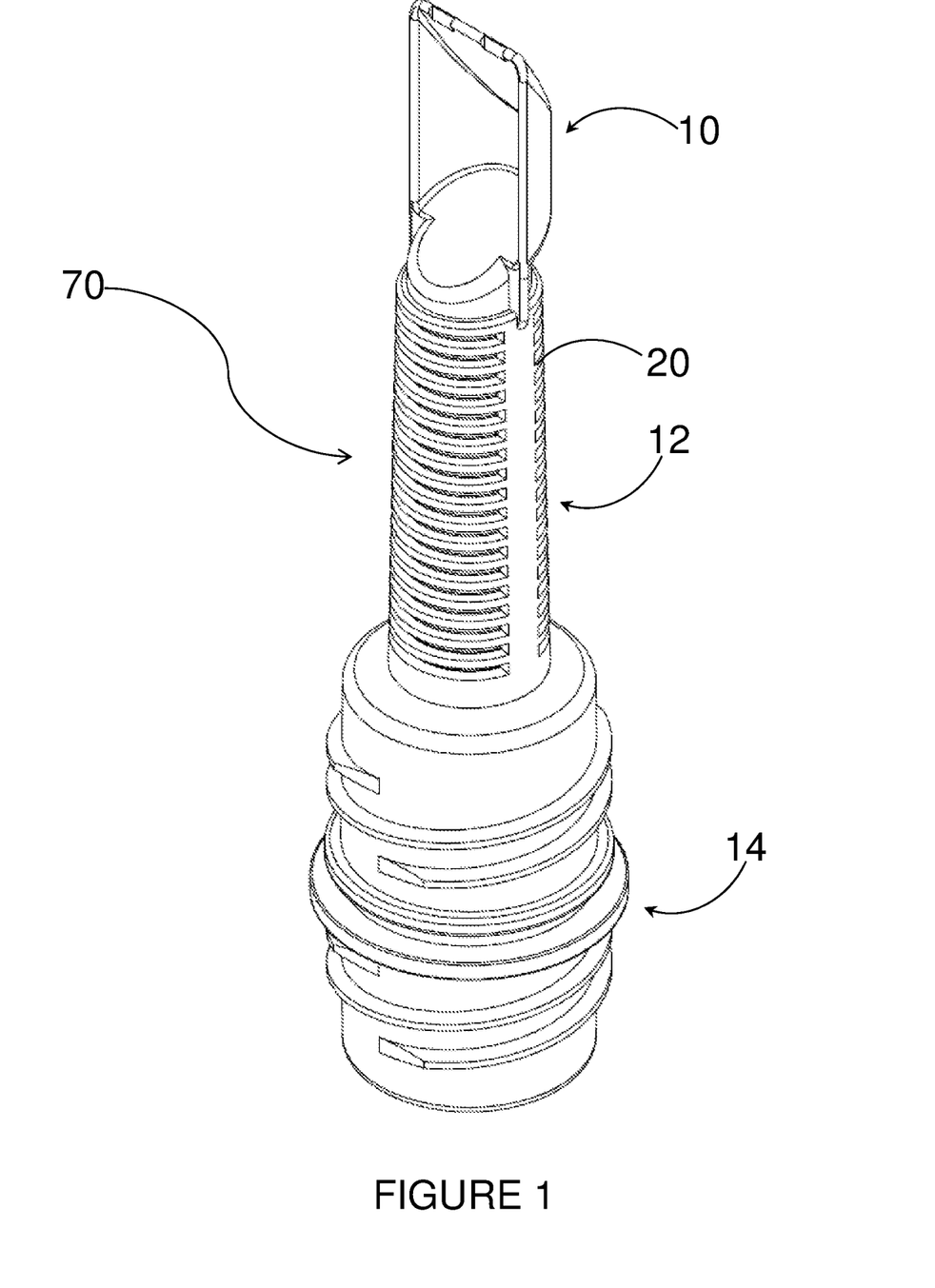
FIG. 1 is perspective view of a filter device according to an embodiment of the invention.
Figure 2:
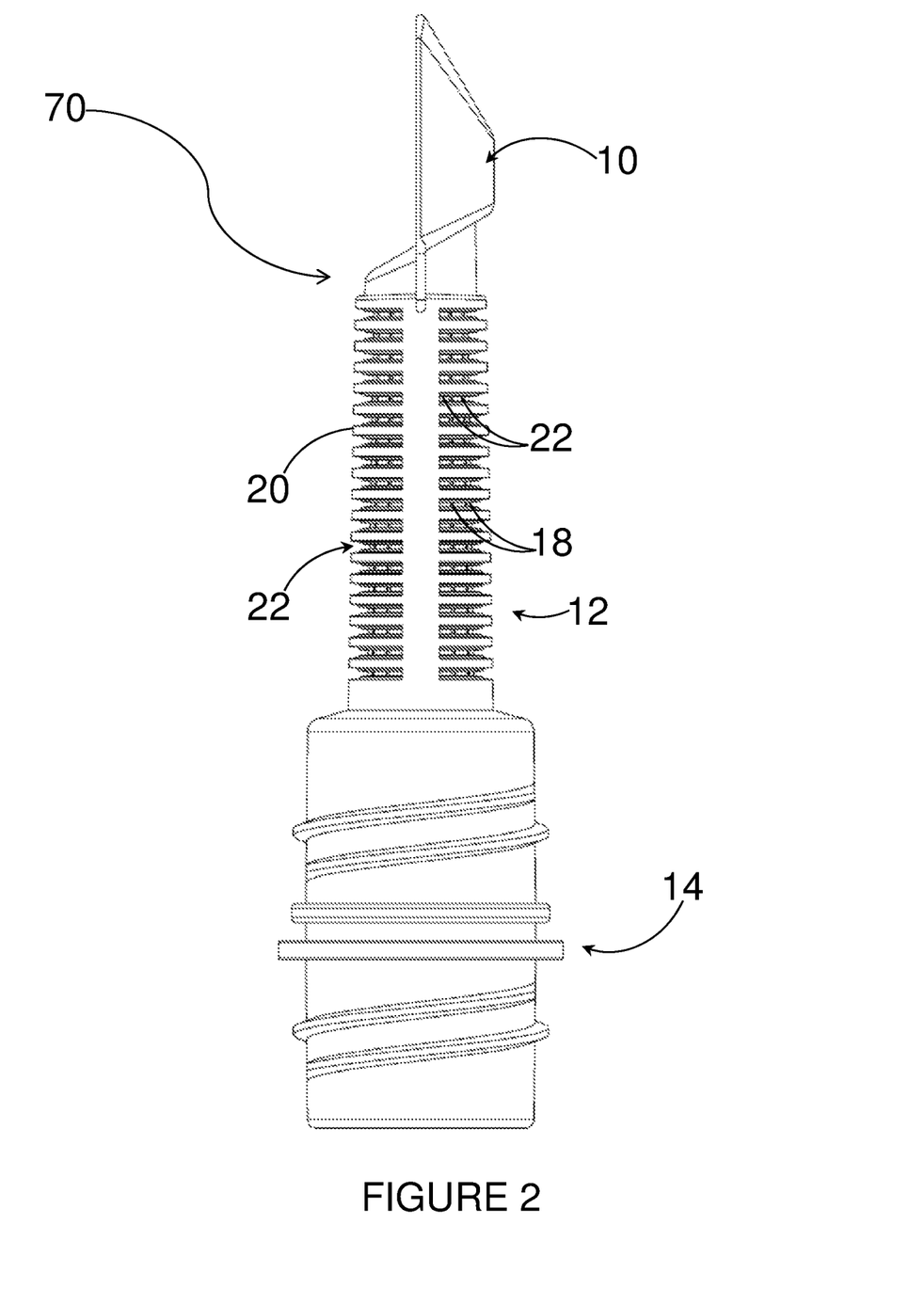
FIG. 2 is a plan view from the side of the filter device of FIG. 1.
Figure 3A:
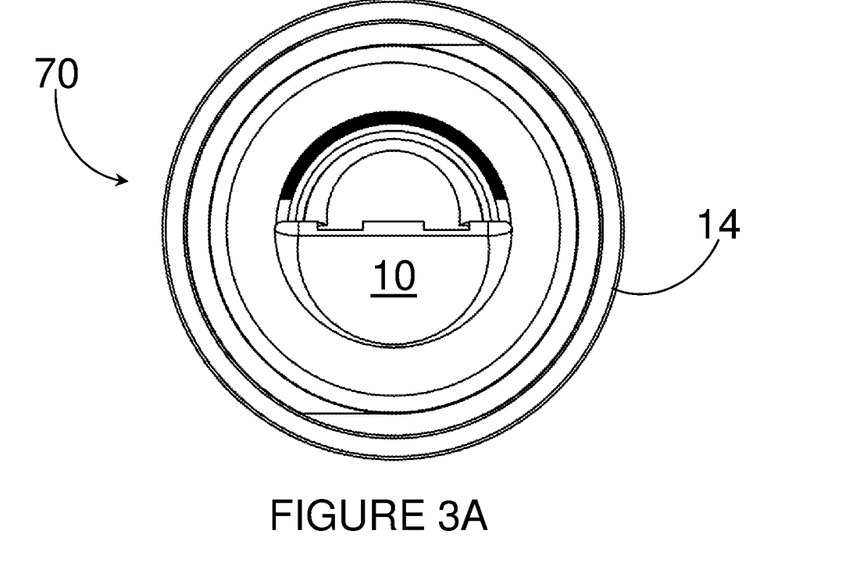
FIG. 3A is a top end view of the filter device of FIG. 1.
Figure 3B:
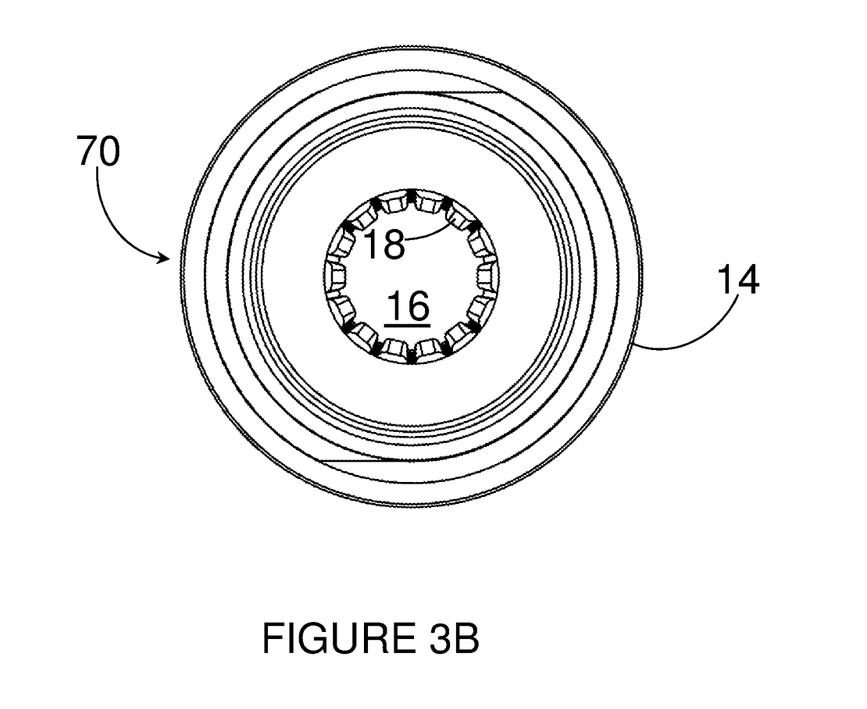
FIG. 3B is a bottom end view of the filter device of FIG. 1.
Figure 4:
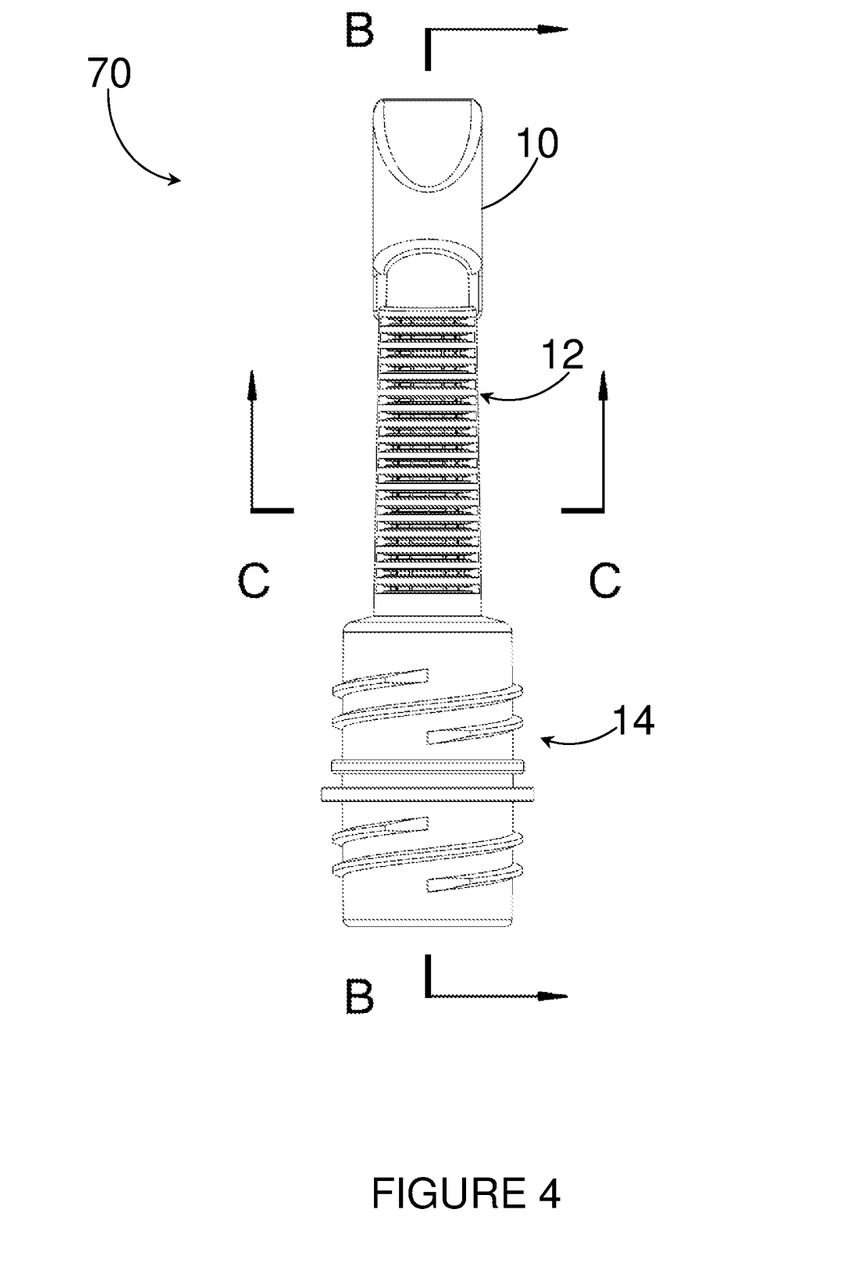
FIG. 4 is a plan view from a rear side of the filter device of FIG. 1, indicating lines BB and CC.
Figure 5A:
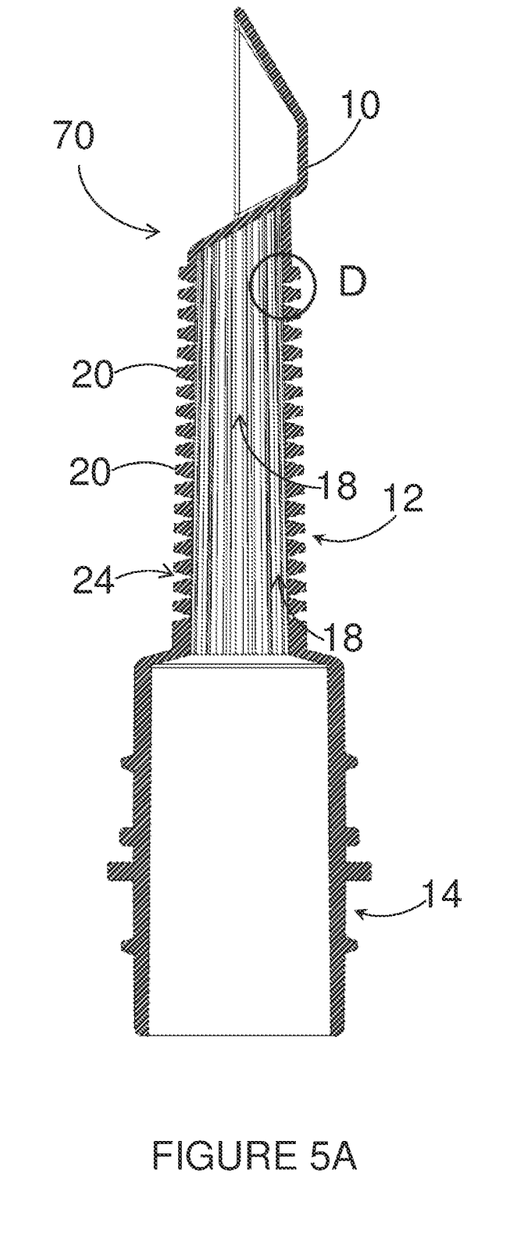
FIG. 5A is a cross-sectional view of the filter device of FIG. 1, taken along the line BB shown in FIG. 4.

The filter device 70 is locatable within the first and second receptacles 80, 90, such that it extends longitudinally within a housing of the filter assembly 100 provided by the first mixing receptacle 80 and the second filtrate receiving receptacle 90. The body 12 of the filter device 70 comprises a lattice structure of crossing internal 18 and external 20 elongated elements. A cross-sectional view of the filter device 70 is shown in FIG. 5A; and in FIG. 5B an enlarged view of part of the image of FIG. 5A is shown. It can be seen that the crossing internal 18 and external 20 elongated elements take the form of crossing internal ribs 18 and external ribs 20 which define an arrangement of external and generally circumferentially extending channels 24 and internal pores 22. The external ribs 20 are presented outwardly of the tube or hollow core of the filter device 70. In other words, with respect to the plane of the pores 22, the external ribs 20 are disposed further outwardly than the internal ribs 18. This can also be seen in FIG. 2. External, and at least partially circumferentially arranged, ribs 20 on the exterior of the lattice structure create a series of channels 24 which act as both a first level filter for larger particles, and which act as additional filter levels for smaller particles in advance of said pores 22, through which only even smaller particles may pass.

The pores 22 of the lattice structure are defined at least in part by said internal ribs 18.

Figure 5B:
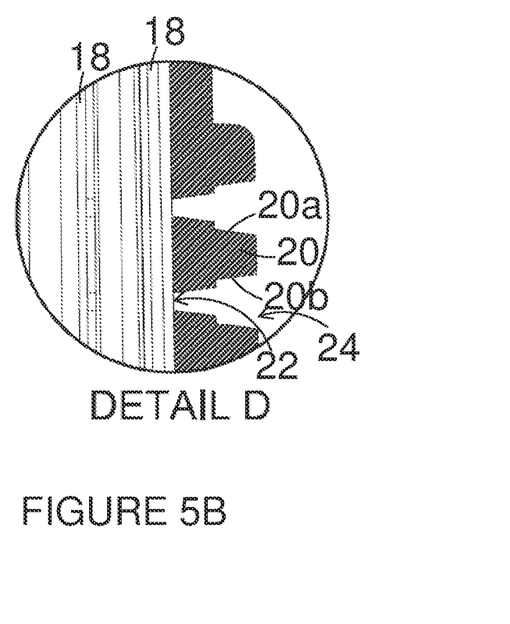
Figure 6A:
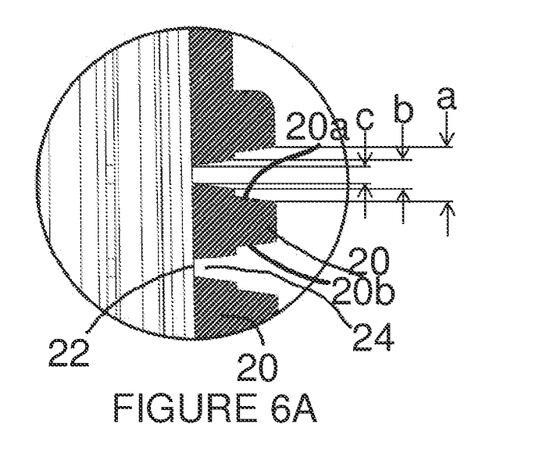
FIG. 6A is the same image as FIG. 5B, annotated to show the maximum, intermediate and minimum widths of opening between two adjacent externally and transversally extending elements of the lattice structure.
Figure 6B:
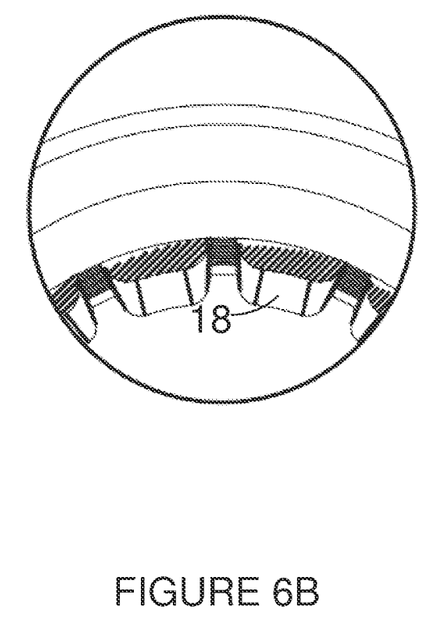
FIG. 6B is an enlarged view of part of the filter device of FIG. 1, showing longitudinally extending internal rib elements that help to make up the lattice structure of the filter device.

FIGS. 5B and 6A show the cross-sectional shape of the external ribs 20, which extend substantially circumferentially about at least a substantial part of the filter device 70. It can be seen that between two adjacent external ribs 20 the channel 24 is formed. The channel 24 is defined by parts of each of said two adjacent external ribs 20 and acts as a first level filter for larger particles and provides one or more additional filter levels for smaller particles in advance of said pores 22.

Optionally and as shown in FIG. 5B, the elongate external ribs have stepped or toothed side walls. The risers of these steps may be parallel with a notional radial axis of the filter device 70 or as shown, the risers of the steps may be acutely angled. The external ribs 20 are shaped and arranged to provide said one or more additional filter levels and this may be achieved in some arrangements by them having one or more side walls 20a, 20b that are shaped in a stepped, castellated or otherwise graded manner in order to facilitate at least three levels of filtration.

As shown in FIG. 6A an external rib 20 has an outer edge and two side walls 20a, 20b. The first and second side walls 20a, 20b are each shaped in a similar stepped manner to one another, such that the external rib 20 is symmetrical in cross-section. As illustrated in FIG. 6A, between two adjacent external ribs 20 an opening 24 is formed which has a maximum outer width (a) between the two front edges of the adjacent ribs 20. Additionally, the opening 24 has a minimum inner width (c) as shown; and one or more intermediate widths (b) between the maximum outer width (a) and the minimum inner width (c). In this arrangement, one additional intermediate width (b) is provided between a step of the first side wall 20a of one rib 20 and the step of the second side wall 20b of the adjacent rib 20. The sides 20a, 20b are not merely tapered towards pore 22, but comprise a distinct step at width (b). In this way the filter assembly 100 is capable of providing at least three levels of filtration. The intermediate width (b) is less than the maximum outer width (a) and is greater than the minimum inner width (c). Optionally, the maximum outer width (a) provides a first level filter of about 1 mm; the intermediate width (b) of the opening 24 formed between two adjacent external ribs 20 comprises a second level filter of about 440 microns; and the minimum inner width (c) provides a third level filter of about 220 microns. The configuration of the channel 24 of the lattice structure 12 formed by the internal ribs 18 and external ribs 20 defines an optional three-level series of successively decreasing pores, whereby particles trapped by the external ribs 20 can confront one or more pores 22 without any observable restriction in the flow of the liquid being filtered through the filter device 70.

The lattice structure disclosed herein allows for the filter device 70 to be injection moulded as a single unit, such that the filter assembly 100 conveniently only comprises three parts 70, 80, 90 which are easily and simply attached together. Because the filter device 70 can close the mixing tube 80 and filtrate receiving tube 90, the filter assembly 100 when closed is configured for forced filtration by centrifuge. Beneficially, the necessity for additional solvent is removed, thus providing a safer filtering system.

In prior art systems, in order to obtain three levels of filtering, more components are required. Beneficially, however, in the present arrangement providing external ribs 20 on the exterior of the lattice which will act as a pre-filter for larger particles in advance of the pores 22; then subsequently a second level of the same providing additional pre filtration; and a third level filter used to finely separate the sample presented and eject it delivering micro-organisms to the lower chamber 90, a filter assembly 100 is provided that is easier to manufacture and assemble, quicker to use and that requires no solvent.

Figure 9:
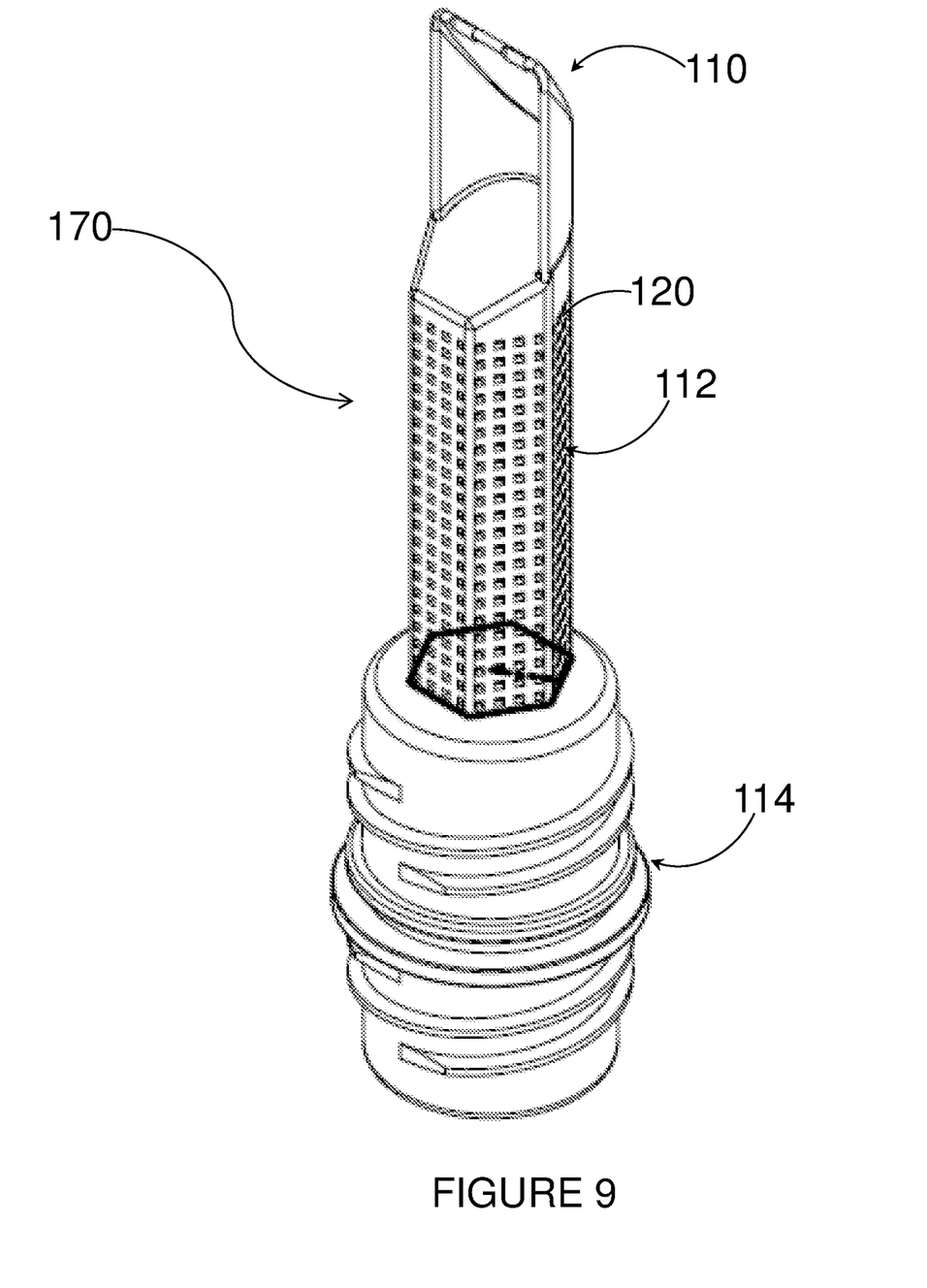
FIG. 9 is a perspective view of a filter device according to another embodiment, wherein the body of the filter device has a generally non-circular cross-sectional shape.
Figure 10A:
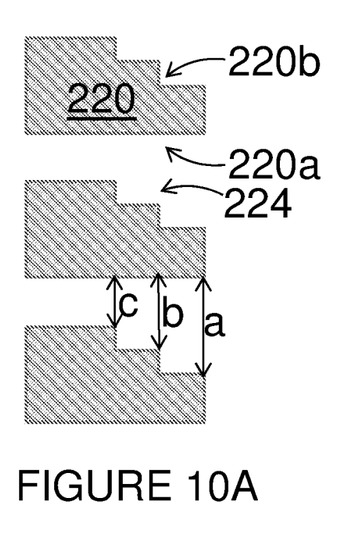
FIGS. 10A and 10B are schematic cross-sectional images of part of an elongate rib of alternative versions of filter device.
Figure 10B:
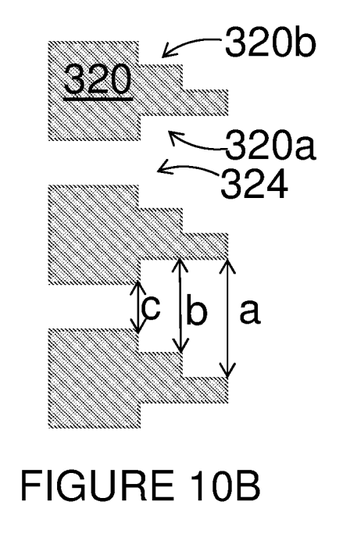

Referring now to FIGS. 9 to 10B there is shown alternative embodiments of the filter assembly or filter device of the present disclosure. In the alternative illustrated embodiments, like numerals have, where possible, been used to denote like parts, albeit with the addition of the prefix "100" and "200" and "300" to indicate that these features belong to the alternative embodiments respectively.

In FIG. 9, there is shown a filter device 170 that comprises a head 110, a body 112 comprising the lattice structure, and a closing portion 114 structured and arranged for fitting into and closing the open ends of the first and second receptacles 80, 90. In this arrangement however, the body 112 comprising the lattice structure has a cross-sectional shape that is not generally circular, but rather has an alternative shape, such as a polygonal shape, more specifically, as shown, the lattice structure has a cross-sectional shape that is hexagonal. It will be appreciated that the generally "circumferentially" extending external ribs, still cross with the internal ribs to form a matrix of pores; and that the external ribs 120 are structured and arranged as described herein to provide three-levels of filtering in a channel having distinct sections of successively decreasing width.

Referring now to FIG. 10A, there is shown a schematic cross-sectional image of part of an elongate rib 220 of a filter device according to various embodiments of the disclosure. The external ribs 220 each have two side walls 220a, 220b. Optionally, neither side wall 220a, 220b is tapered, though in other arrangements, one or both side walls 220a, 220b, may be tapered. Here, one side wall 220a is substantially flat or straight (in other words, not stepped), and the other side wall 220b is shaped in a stepped manner such that between two adjacent external ribs 220 an opening 224 is formed which has a maximum outer width (a), a minimum inner width (c) and one or more widths (b) therebetween. In this way the filter assembly is capable of providing at least three levels of filtration. In this arrangement, the step-shaped side wall 220b comprises three "risers", two "treads" and a front edge to create, the three distinctly sized sections of the channel 224 such that filtration in three successive size increments is provided using channels 224 defined by asymmetric external ribs 220.

Referring now to FIG. 10B, there is shown a schematic cross-sectional image of part of an elongate rib 320 of a filter device according to various embodiments of the disclosure. The external ribs 320 each have two side walls 320a, 320b. Optionally, neither side wall 320a, 320b is tapered, though in other arrangements, one or both side walls 320a, 320b, may be tapered (optionally inwardly toward the pore (not shown)). Here, one side wall 320a is shaped in a first stepped manner, and the other side wall 320b is shaped in a second stepped manner, the two side walls 320a, 320b being differently shaped, such that between two adjacent external ribs 320 an asymmetric opening or channel 324 is formed which has a maximum outer width (a), a minimum inner width (c) and one or more widths (b) therebetween. In this way the filter assembly is capable of providing at least three levels of filtration. In this arrangement, the first step-shaped side wall 320b comprises three "risers" and two "treads"; and the second step-shaped side wall 320a comprises two "risers" and one "tread", to create the three distinctly sized sections of the channel 324 such that filtration in three successive size increments is provided using channels 324 defined by asymmetric external ribs 320.

It can be appreciated that various changes may be made within the scope of the present invention, for example, the elongate ribs may not be symmetrical in form.

The invention claimed is:
1. A filter assembly comprising
a tubular housing comprising:
   a first receptacle having an open end and a closed end; and
   a second receptacle having an open end and a closed end; and
a filter device arranged to extend longitudinally within the tubular housing, wherein the filter device has a closed end located in the first receptacle and an open end located in the second receptacle and the second receptacle is configured to receive filtrate from the filter device,
wherein:
   the filter device comprises a lattice structure of crossing internal elongated elements and external elongated elements that define an arrangement of pores located in the first receptacle;
   each one of the external elongated elements comprises a first side wall and a second side wall;
   the first side wall of one of the external elongated elements faces the second side wall of an adjacent one of the external elongated elements such that a channel is formed between the first side wall and the second side wall to filter particles in advance of the pores;
   the first side wall of each one of the external elongated elements comprises a step such that the channel has an inner width, an outer width, and intermediate width between the inner width and the outer width such that the channel provides three levels of filtration;
   the outer width of the channel provides a first level filter for first particles;
   the intermediate width of the channel is less than the outer width of the channel and provides a second level filter for second particles; which are smaller than the first particles; and
   the inner width of the channel is less than the intermediate width of the channel and provides a third level filter for third particles, which are smaller than the second particles.

2. The filter assembly of claim 1, wherein the lattice structure of crossing internal elongated elements and external elongated elements comprises:
 internal ribs extending longitudinally in a direction from the closed end of the filter device to the open end of the filter device; and
 external ribs extending transversely to the internal ribs.

3. The filter assembly of claim 2, wherein said pores of the lattice structure are defined at least in part by the internal ribs.

4. The filter assembly of claim 2, wherein the external ribs extend substantially circumferentially about the filter device.

5. The filter assembly of claim 1, wherein the channel is in fluid communication with at least a portion of the pores.

6. The filter assembly according to claim 5, wherein the second side wall of at least one of the external elongated elements is substantially flat such that the channel has the outer width, the inner width, and the intermediate width between the outer width and the inner width.

7. The filter assembly according to claim 1, wherein the second side wall of at least one of the external elongated elements comprises a second step such that the channel has the outer width, the inner width, and the intermediate width between the outer width and the inner width.

8. The filter assembly according to claim 1, wherein the first side wall of at least one of the external elongated elements comprises a third step such that the channel has the outer width, the inner width, the intermediate width and a second intermediate width such that the channel provides four levels of filtration,
 wherein the second intermediate width of the channel is less than the intermediate width of the channel and larger than the inner width of the channel and provides a fourth level filter for fourth particles which are smaller than the second particles and larger than the third particles.

9. The filter assembly according to claim 1, wherein:
 the outer width of the channel is about 1 mm;
 the intermediate width of the channel is about 440 microns; and
 the inner width of the channel about 220 microns.

10. The filter assembly according to claim 1, wherein the first side wall of one of the external elongated elements and the second side wall of an adjacent one of the external elongated elements have different shapes such that the channel is asymmetric.

11. The filter assembly according to claim 1, wherein the filter device is situated to close the open end of the first receptacle and the open end of the second receptacle, such that the filter assembly, when closed, is configured for forced filtration by centrifuge.

12. The filter assembly according to claim 1, wherein the filter device further comprises a head, a body comprising the lattice structure, and a closing portion structured and arranged for fitting into and closing the open end of the first receptacle and the open end of the second receptacle, wherein the body comprising the lattice structure has a cross-sectional shape taken in a plane through the external elongated elements of the lattice structure that is generally circular, hexagonal or another polygonal shape.

13. The filter assembly according to claim 1, wherein the first side wall of one of the external elongated elements and the second side wall of an adjacent one of the external elongated elements have the same shape such that the channel is symmetric.

* * * * *